United States Patent
Lim et al.

(10) Patent No.: US 11,208,671 B2
(45) Date of Patent: Dec. 28, 2021

(54) RECOMBINANT CELL AND METHOD OF PRODUCING ITACONIC ACID

(71) Applicant: City University of Hong Kong, Kowloon (HK)

(72) Inventors: Chee Kent Lim, Sabah (MY); Patrick Kwan Hon Lee, New Territories (HK)

(73) Assignee: City University of Hong Kong, Kowloon (HK)

( * ) Notice: Subject to any disclaimer, the term of this patent is extended or adjusted under 35 U.S.C. 154(b) by 0 days.

(21) Appl. No.: 16/509,794

(22) Filed: Jul. 12, 2019

(65) Prior Publication Data

US 2021/0010039 A1    Jan. 14, 2021

(51) Int. Cl.
*C12P 7/46* (2006.01)
*C12N 15/63* (2006.01)

(52) U.S. Cl.
CPC .............. *C12P 7/46* (2013.01); *C12N 15/63* (2013.01); *C12Y 401/01006* (2013.01)

(58) Field of Classification Search
CPC .... C12P 7/46; C12N 15/63; C12Y 401/01006
See application file for complete search history.

(56) References Cited

U.S. PATENT DOCUMENTS

2010/0285546 A1   11/2010 Liao
2015/0315599 A1*  11/2015 Shetty .............. C12P 7/40
                                                    435/6.18

FOREIGN PATENT DOCUMENTS

CN    107723317    2/2018
KR    20170060952  6/2017
WO    2014161988   10/2014

OTHER PUBLICATIONS

Witkowski et al., Biochemistry 38:11643-11650, 1999.*
Tang et al., Phil Trans R Soc B 368:20120318, 1-10, 2013.*
Seffernick et al. (J. Bacteriol. 183(8):2405-2410, 2001.*
Branden et al., Introduction to Protein Structure, Garland Publishing Inc., New York, p. 247, 1991.*
Sadowski et al., Current Opinion in Structural Biology 19:357-362, 2009.*
Lim et al., Engineering methylotrophic bacteria for the production of itaconic acid from renewable simple carbon sources; M68 poster presented on May 1, 2017 at the 39th Symposium on Biotechnology for Fuels and Chemicals, San Francisco, CA.*
Korotkova et al., Gen Bank accession No. AF287907, Mar. 18, 2005.*
Sonntag et al., Metabolic Engineering 32:82-94, 2015.*
Zhao et al., GenBank accession No. MH298057, May 19, 2018.*
Marx et al., Microbiology 147:2065-2075, 2011.*
El-Iman, et al, "Fermentative Itaconic Acid Production". J Biodiversity, Bioprospecting and Development, 2014, 1:119.
Hajian, H., et al, "Itaconic Acid Production by Microorganisms: A Review" Current Research Journal of Biological Sciences, 2015, 7:37-42.
Zhang, W., et al "Current Advance in Bioconversion of Methanol to Chemicals", Biotechnology for Biofuels, 2018, 11, 260.
Bafana R., et al, "New approaches for itaconic acid production: bottlenecks and possible remedies", Critical Reviews in Biotechnology, 2018, 38. 68-82.

* cited by examiner

*Primary Examiner* — Delia M Ramirez
(74) *Attorney, Agent, or Firm* — Renner Kenner Greive Bobak Taylor & Weber

(57) ABSTRACT

A recombinant cell and a method of producing itaconic acid using such recombinant cell. The recombinant cell is of the genus *Methylorubrum* and includes a first polynucleotide sequence as defined in SEQ ID NO: 1 or a homologue thereof operably linked to a regulatory sequence.

18 Claims, 9 Drawing Sheets

Specification includes a Sequence Listing.

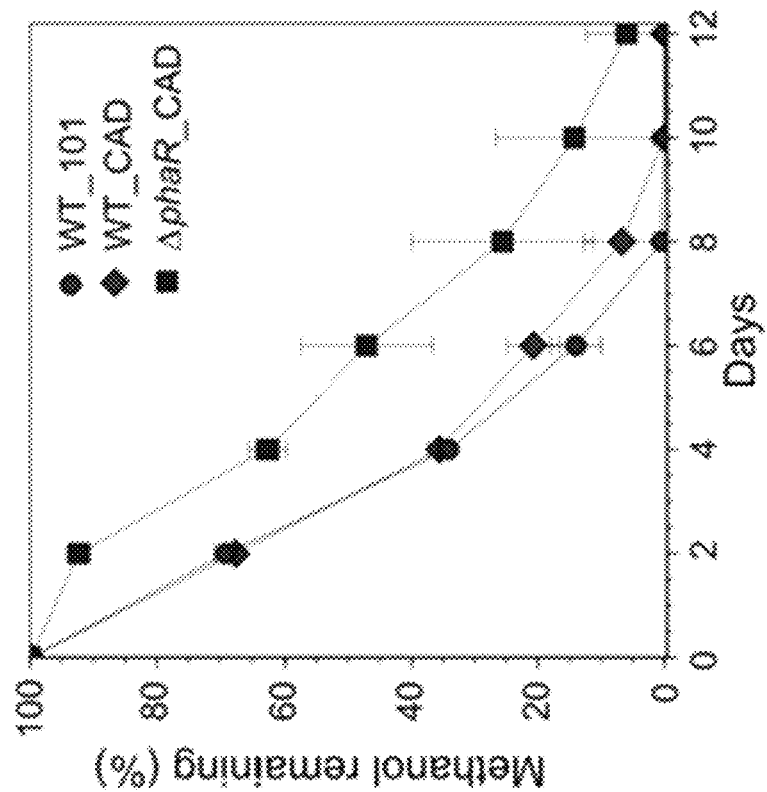
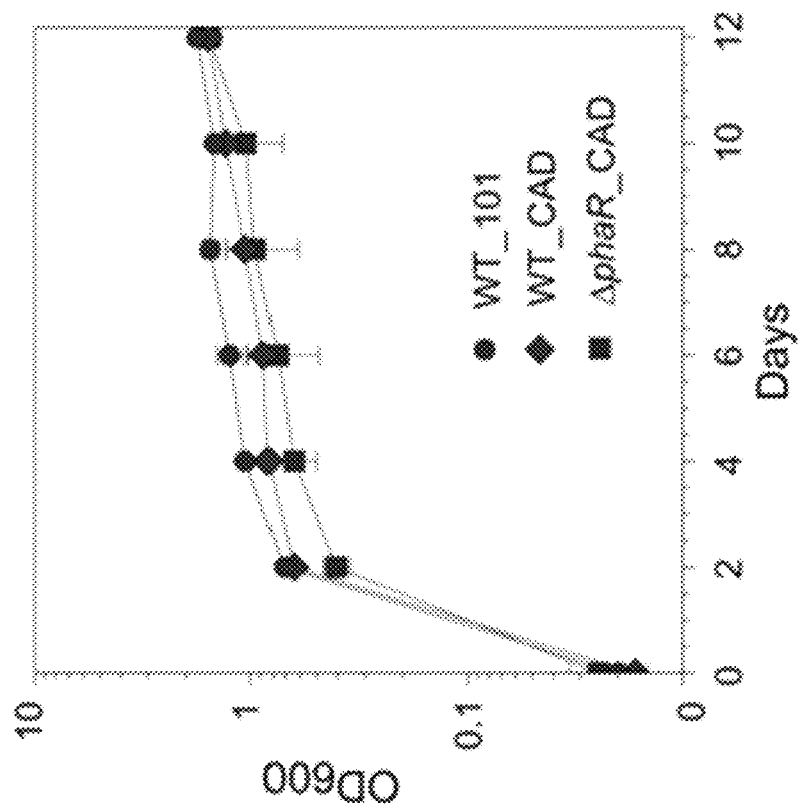
Fig. 6A
Fig. 6B

RECOMBINANT CELL AND METHOD OF PRODUCING ITACONIC ACID

SEQUENCE LISTING

The Sequence Listing file entitled "sequencelisting" having a size of 9,184 bytes and a creation date of Jul. 12, 2019, that was filed with the patent application is incorporated herein by reference in its entirety

TECHNICAL FIELD

The present invention relates to a recombinant cell and a method of producing itaconic acid using such a recombinant cell. Particularly, the invention pertains to a recombinant cell of the genus *Methylorubrum*.

BACKGROUND OF THE INVENTION

Itaconic acid, a C-5 dicarboxylic organic acid, is a high-value polymer building block with broad application in various industries. Polymers derived from itaconic acid have wide-ranging industrial uses, including as ingredients for making superabsorbent polymers, as co-builders in detergents, and anti-scaling agents in water treatment processes to name a few. In view of its role as an important pre-cursor to various products, maximizing itaconic acid production is of commercial value.

Conventionally, itaconic acid production is by fermentation with *Aspergillus terreus* is expensive and with undesirable characteristics in cultivation such as spore formation, susceptibility to damage by shear stress and filamentous growth. Other deficiencies when relying on the conventional method of producing itaconic acid is that *Aspergillus terreus* grows slowly and does not produce itaconic acid in its spore-forming stage.

Accordingly, there is a strong need for a method that produces itaconic acid inexpensively and in high yield.

SUMMARY OF THE INVENTION

In a first aspect, the present invention pertains to a recombinant cell that comprises a first polynucleotide sequence as defined in SEQ ID NO: 1 or a homologue thereof operably linked to a regulatory sequence, wherein the recombinant cell is of the *Methylorubrum* genus.

In one embodiment, the recombinant cell comprises a second polynucleotide sequence as defined in SEQ ID NO: 2 or a homologue thereof.

In one embodiment, the first polynucleotide sequence encodes a protein or fragment thereof having cis-aconitic decarboxylase (CAD) activity for producing itaconic acid from a carbon substrate.

In one embodiment, the carbon substrate is selected from a group comprising of methanol, methylamine, formate, pyruvate, succinate, lactate and acetate.

In one embodiment, the carbon substrate is selected from a group consisting of acetate, succinate and methanol.

In one embodiment, the carbon substrate is methanol.

In one embodiment, the recombinant cell is *Methylorubrum extorquens*.

In one embodiment, the recombinant cell is *Methylorubrum extorquens* AM1.

In one embodiment, the regulatory sequence is a constitutive or strong promoter as defined in SEQ ID NO: 3 or a homologue thereof.

In one embodiment, the CAD is one derivable from or found in *Aspergillus terreus*.

Turning to a second aspect, the present invention pertains to a method of producing itaconic acid using a recombinant cell, wherein the recombinant cell comprises a first polynucleotide sequence as defined in SEQ ID NO: 1 or a homologue thereof operably linked to a regulatory sequence, wherein the recombinant cell is of the genus *Methylorubrum*.

In one embodiment of the second aspect, the further comprises a second polynucleotide sequence as defined in SEQ ID NO: 2 or a homologue thereof.

In one embodiment of the second aspect, the first polynucleotide sequence or second polynucleotide sequence has at least 80% sequence identity with the sequence of SEQ ID NO: 1 or SEQ ID NO: 2, respectively.

In one embodiment of the second aspect, the first polynucleotide sequence encodes a protein or fragment thereof having CAD activity for producing itaconic acid.

In one embodiment, the method further comprises a step of incubating the recombinant cell in a medium containing a carbon substrate for producing itaconic acid.

In one embodiment of the second aspect, the carbon substrate is selected from a group comprising of methanol, methylamine, formate, pyruvate, succinate, lactate and acetate.

In one embodiment of the second aspect, the carbon substrate is selected from a group consisting of acetate, succinate and methanol.

In one embodiment of the second aspect, the carbon substrate is methanol.

In one embodiment of the second aspect, the recombinant cell is *Methylorubrum extorquens*.

In one embodiment of the second aspect, the recombinant cell is *Methylorubrum extorquens* AM1.

In one embodiment of the second aspect, the regulatory sequence is a constitutive or strong promoter as defined in SEQ ID NO: 3 or a homologue thereof.

In one embodiment of the second aspect, the CAD is one derivable from or found in *Aspergillus terreus* and the method further comprises fermenting the recombinant cell in a suitable fermentation medium to produce itaconic acid.

Those skilled in the art will appreciate that the invention described herein is susceptible to variations and modifications other than those specifically described. The invention includes all such variations and modifications. The invention also includes all steps and features referred to or indicated in the specification, individually or collectively, and any and all combinations of the steps or features.

Other features and aspects of the invention will become apparent by consideration of the following detailed description and accompanying drawings.

BRIEF DESCRIPTION OF DRAWINGS

FIG. 6A is a line graph showing optical density ($OD_{600}$) in WT_101, WT_CAD, and ΔphaR_CAD strains of *Methylorubrum extorquens* AM1 grown in HM medium supplemented with 240 mM methanol as the carbon substrate in accordance with an example embodiment.

FIG. 6B is a line graph showing methanol remaining (%) in WT_101, WT_CAD, and ΔphaR_CAD strains of *Methylorubrum extorquens* AM1 grown in HM medium supplemented with 240 mM methanol as the carbon substrate in accordance with an example embodiment.

Figure 1:
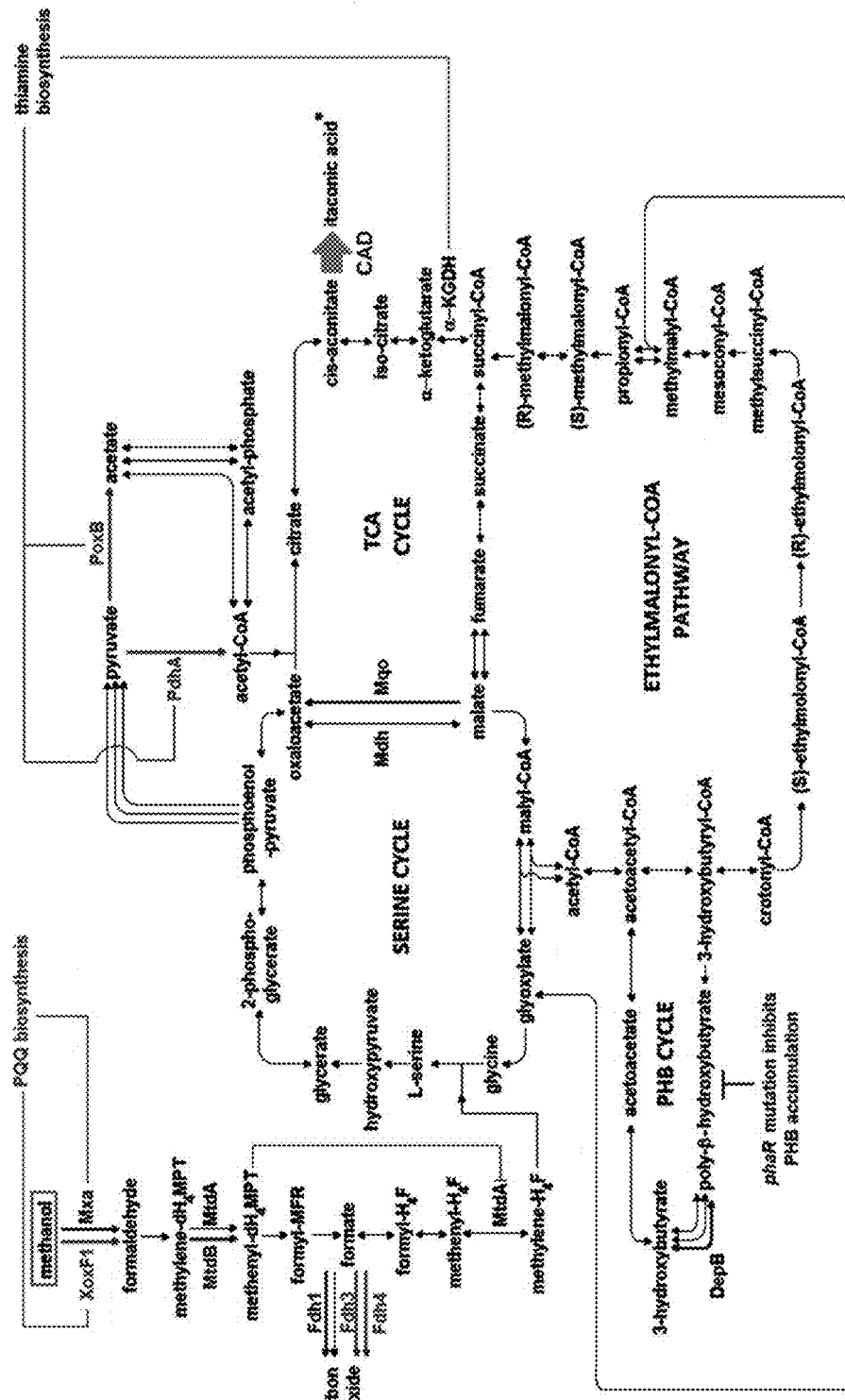
FIG. 1 is a schematic diagram illustrating carbon metabolic pathways in the formation of itaconic acid.

Those skilled in the art will appreciate that the invention described herein is susceptible to variations and modifications other than those specifically described. The invention includes all such variations and modifications. The invention also includes all steps and features referred to or indicated in the specification, individually or collectively, and any and all combinations of the steps or features.

Other features and aspects of the invention will become apparent by consideration of the following detailed description and accompanying drawings.

DETAILED DESCRIPTION OF EMBODIMENTS

Unless otherwise defined, all technical terms used herein have the same meaning as commonly understood by one skilled in the art to which the invention belongs.

As used herein, "comprising" means including the following elements but not excluding others. "Essentially consisting of" means that the material consists of the respective element along with usually and unavoidable impurities such as side products and components usually resulting from the respective preparation or method for obtaining the material such as traces of further components or solvents. The expression that a material is certain element is to be understood for meaning "essentially consists of" said element. As used herein, the forms "a," "an," and "the," are intended to include the singular and plural forms unless the context clearly indicates otherwise.

In the first aspect, the present invention pertains to a recombinant cell including a first polynucleotide sequence as defined in SEQ ID NO: 1 or a homologue thereof operably linked to a regulatory sequence.

The genus of the cell used in the present invention may include, but are not limited to, *Aspergillus, Citrobacter, Corynebacterium, Escherichia, Lactobacillus, Lactococcus, Synechocystis, Saccharomyces, Pectobacterium, Salmonella, Methylorubrum, Methylobacterium, Methylomicrobium, Gluconobacter, Rhodopseudomonas, Clostridium, Pseudomonas*. In a preferred embodiment the recombinant cell is of the genus *Methylorubrum*. More preferably the recombinant cell is *Methylorubrum extorquens*, and most preferably the recombinant cell is *Methylorubrum extorquens* AM1.

The term "recombinant" as used herein means that the cell, preferably a bacterium, comprises a foreign nucleic acid molecule such as a plasmid which does not exist naturally in the non-genetically modified cell, i.e. the wild type cell. The foreign nucleic acid molecule may be in a form of a recombinant plasmid which comprises different genetic elements in a specific combination or arrangement. The recombinant plasmid is then inserted into a cell for example through infection. The transcription of the recombinant plasmid allows the transcription of the foreign nucleic acid and thus may result in expression of the foreign nucleic acid. A person skilled in the art would appreciate suitable methods for introducing the recombinant vector into a cell for infection.

In this invention, a recombinant plasmid, an expression vector, carrying the first polynucleotide and other genetic elements has been introduced into the recombinant cell through transformation. Preferably, the recombinant plasmid in the present invention is carrying a first polynucleotide as defined in SEQ ID NO: 1 or a homologue thereof operably linked to a regulatory sequence.

The first polynucleotide preferably encodes a protein or fragment having cis-aconitic decarboxylase (CAD) activity. The first polynucleotide is most preferably a codon-optimized CAD polynucleotide sequence that has been subjected to codon optimization based on the optimal codon usage in the recombinant cell. CAD is an enzyme that converts the reaction of cis-aconitic acid to itaconic acid as below.

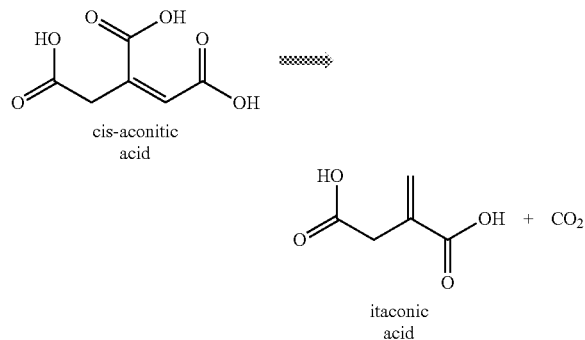

The term cis-aconitic decarboxylase or CAD as used herein refers to any naturally occurring CADs and functional equivalents thereof. Preferably, the CAD is one derivable from or found in *Aspergillus terreus*. SEQ ID NO: 4 is an amino acid sequence of an exemplary *Aspergillus terreus* CAD (BAG49047.1).

In a further example embodiment, the recombinant cell may be transfected with a recombinant plasmid carrying the first polynucleotide as defined in SEQ ID NO: 1 or a homologue thereof operably linked to a regulatory sequence. The recombinant cell may comprise a further second polynucleotide as defined in SEQ ID NO: 2 or a homologue thereof in its chromosome. Most preferably, the second polynucleotide encodes a mutant regulator gene phaR truncated from nucleotide position of 269 to 599 (by excising 339 base pairs out of the entire gene length of 612 base pairs). In an example embodiment, the second polynucleotide has an amino acid sequence as defined in SEQ ID NO: 9 or a homologue thereof.

Referring back to the recombinant plasmid, the recombinant plasmid of the present invention is artificially synthesized by inserting a cassette comprising the first polynucleotide as described above to an expression vector. Both the plasmid and the cassette have at least two restriction sites to be cleaved by a restriction enzyme. The cleaved plasmid and cassette are then ligated together by using a ligase and form the recombinant plasmid.

In an embodiment, the recombinant cell includes a first polynucleotide sequence as defined in SEQ ID NO: 1 or a homologue thereof and/or a second polynucleotide sequence as defined in SEQ ID NO: 2 or a homologue thereof. The term "homologue thereof" refers to a functional equivalent of the first polynucleotide sequence or the second polynucleotide sequence, i.e. nucleotides having a sequence identity of at least 50%, at least 60%, at least 70%, at least 80%, at least 90% or at least 95% to the first or second polynucleotide sequence as defined by SEQ ID NO: 1 or SEQ ID NO: 2, respectively, according to the present invention. In an embodiment, a homologue of the first polynucleotide sequence or second polynucleotide sequence has at least 80% sequence identity with the sequence of SEQ ID NO: 1 or SEQ ID NO: 2, respectively. In an embodiment, a homologue of the first polynucleotide sequence or second polynucleotide sequence has at least 90%, 91%, 92%, 93%, 94%, 95%, 96%, 97%, 98%, or 99% overall sequence identity with the sequence of SEQ ID NO: 1 or SEQ ID NO: 2, respectively. In a particular embodiment, the recombinant cell consists of a sequence of SEQ ID NO: 1 or SEQ ID NO: 2 or a sequence of SEQ ID NO: 1 and ID NO: 2, or a homologue thereof.

The term "regulatory sequence" as used herein includes a promoter. The promoter refers to a genetic element on the recombinant plasmid that is capable of initiating the transcription of the polynucleotide inserted into the plasmid and/or other sequences on the plasmid. At a minimum, a promoter contains an RNA polymerase binding site. It can further contain one or more enhancer elements which, by definition, enhance transcription, or one or more regulatory elements that control the on/off status of the promoter. The promoter may be a constitutive or strong promoter.

In an embodiment the first polynucleotide sequence encodes a protein or fragment thereof having CAD activity for producing itaconic acid from a carbon substrate. The recombinant cell utilizes the carbon substrate to produce itaconic acid. The carbon substrate as used herein includes C-1 molecules or multi-carbon molecules.

The carbon substrate is selected from a group that includes methanol, methylamine, formate, pyruvate, succinate, lactate and acetate. Preferably, the carbon substrate is selected from a group that includes acetate, succinate and methanol.

Most preferably, the carbon substrate is methanol. The use of methanol as a carbon substrate for producing itaconic acid advantageously allows for the production of itaconic acid, a high value polymer building block, from a low-cost renewable feedstock whose production does not compete food supply, while being a substrate with low biotic contamination risk.

In another aspect, there is provided a method of producing itaconic acid using a recombinant cell. Particularly, a method of producing itaconic acid using a recombinant cell as previously described, specifically wherein the recombinant cell includes a first polynucleotide sequence as defined in SEQ ID NO: 1 or a homologue thereof operably linked to a regulatory sequence. Preferably, the recombinant cell is a methylotrophic bacterium. Even more preferably, the recombinant cell is of the genus *Methylorubrum*.

In an embodiment, the method further comprises a step of incubating the recombinant cell in a medium containing a carbon substrate for producing itaconic acid. The carbon substrate can be selected from methanol, methylamine, formate, pyruvate, succinate, lactate and acetate. Preferably, the carbon substrate is selected from acetate, succinate and methanol. Most preferably, the carbon substrate is methanol.

In an embodiment, the method includes fermenting the recombinant cell in a suitable fermentation medium to produce itaconic acid. The fermentation medium contains the carbon substrate as described above for supplying sufficient feedstock for conversion.

Accordingly, the invention beneficially provides a novel and effective recombinant cell of the genus *Methylorubrum* including a first polynucleotide sequence as defined in SEQ ID NO: 1 or a homologue thereof operably linked to a regulatory sequence wherein the first polynucleotide sequence encodes a protein or fragment thereof having cis-aconitic decarboxylase (CAD) activity for producing itaconic acid from a carbon substrate. The recombinant cell as described uses various carbon substrates including acetate, succinate and methanol to produce itaconic acid. The use of inexpensive carbon substrates such as methanol and use of a successfully engineered recombinant cell, most preferably a *Methylorubrum extorquens* bacterium, provides an inexpensive, efficient and effective method of producing itaconic acid. The present invention provides a comparatively inexpensive yet effective alternative to the production of itaconic acid by fermentation with *Aspergillus terreus*.

The invention is now described in the following non-limiting examples.

EXAMPLES

Example 1

Culture Conditions of *Methylorubrum extorquens* AM1 Strains

*Methylorubrum extorquens* AM1 (ATCC 14718) was purchased from the American Type Culture Collection (ATCC). MC, MM, HM and CM media were utilized. MC medium was adapted from Zhu et al. with minor modifications (Zhu, W. L., Cui, J. Y., Cui, L. Y., Liang, W. F., Yang, S., Zhang, C., and Xing, X. H. (2016). Bioconversion of methanol to value-added mevalonate by engineered *Methylobacterium extorquens* AM1 containing an optimized mevalonate pathway. Appl Microbiol Biotechnol 100, 2171-2182. doi: 10.1007/s00253-015-7078-z); MM medium was adapted from ATCC 1057 medium with minor modifications (ATCC 1057 medium www.atcc.org/~/media/B6DAA578E54A4E31A0E80031E1DFB83B.ashx); HM medium was adapted from Mokhtari-Hosseini et al. with minor modifications (Mokhtari-Hosseini, Z. B., Vasheghani-Farahani, E., Heidarzadeh-Vazifekhoran, A., Shojaosadati, S. A., Karimzadeh, R., and Khosravi Darani, K. (2009). Statistical media optimization for growth and PHB production from methanol by a methylotrophic bacterium. Bioresour Technol 100, 2436-2443. doi: 10.1016/j.biortech.2008.11.024); and CM medium was adapted from Choi et al. with minor modifications (Choi, J. H., Kim, J. H., and Lebeault, J. M., (1989). Optimization of growth medium and poly-β-hydroxybutyric acid production from methanol in *Methylobacterium organophilum*. Kor J Appl Microbiol Bioeng 17, 392-396).

AM1 was grown in the minimal medium (MC as shown in Table 1 below) as 25 mL culture in 125 mL-serum bottles containing 124 mM methanol at 30° C. with shaking at 200 rpm. The bottles were loosely capped to allow exchange of atmospheric gases. Other minimal media utilized were HM, CM, and MM as shown in Tables 2, 3 and 4, respectively.

TABLE 1

Composition of minimal media (MC)
a) MC medium

| Solution | Preparation† | Final concentration |
|---|---|---|
| X | In 499 mL H$_2$O | |
| (NH$_4$)$_2$SO$_4$ | 1 g | 1 g/L |
| MgSO$_4$•7H$_2$O | 0.449 g | 0.449 g/L |
| CaCl$_2$•2H$_2$O | 0.0032 g | 0.0032 g/L |
| Y | In 50 mL H$_2$O | |
| Na$_3$C$_6$H$_5$O$_7$•2H$_2$O | 0.671 g | 0.01342 g/L |
| ZnSO$_4$•7H$_2$O | 0.0173 g | 0.0146 g/L |
| MnCl$_2$•4H$_2$O | 0.0099 g | 0.198 mg/L |
| FeSO$_4$•7H$_2$O | 0.25 g | 0.005 g/L |
| Na$_2$MoO$_4$•2H$_2$O | 0.0242 g | 0.484 mg/L |
| CuCl$_2$•2H$_2$O | 0.0085 g | 0.17 mg/L |
| CoCl$_2$•6H$_2$O | 0.0238 g | 0.476 mg/L |
| Na$_2$WO$_4$•2H$_2$O | 0.0054 g | 0.108 mg/L |
| H$_3$BO$_3$ | 0.0015 g | 0.03 mg/L |
| Z | In 500 mL H$_2$O | |
| KH$_2$PO$_4$ | 1.3051 g | 1.3051 g/L |
| Na$_2$HPO$_4$•2H$_2$O | 2.6699 g | 2.6699 g/L |

†499 mL of X was mixed with 1 mL of Y and autoclaved, while 500 mL of Z was adjusted to pH 6.8 and autoclaved. After cooling, 500 mL of X + Y was combined with 500 mL of Z.

TABLE 2

Composition of CM media
b) CM medium

| Solution | Preparation† | Final concentration |
|---|---|---|
| K | In 499 mL H$_2$O | |
| (NH$_4$)$_2$SO$_4$ | 1.0 g | 1 g/L |
| MgSO$_4$•7H$_2$O | 0.45 g | 0.45 g/L |
| CaCl$_2$•2H$_2$O | 0.0033 g | 3.3 mg/L |
| FeSO$_4$•7H$_2$O | 0.0013 g | 1.3 mg/L |
| L | In 50 mL H$_2$O | |
| MnCl$_2$•4H$_2$O | 0.005 g | 0.1 mg/L |
| Na$_2$MoO$_4$•2H$_2$O | 0.002 g | 40 μg/L |
| CuCl$_2$•2H$_2$O | 0.0014 g | 27 μg/L |
| CoCl$_2$•6H$_2$O | 0.002 g | 40 μg/L |
| ZnSO$_4$•7H$_2$O | 0.0065 g | 130 μg/L |
| M | In 500 mL H$_2$O | |
| KH$_2$PO$_4$ | 1.305 g | 1.305 g/L |
| Na$_2$HPO$_4$•2H$_2$O | 2.70 g | 2.70 g/L |

†499 mL of K was mixed with 1 mL of L and autoclaved, while 500 mL of M was adjusted to pH 6.8 and autoclaved. After cooling, 500 mL of K + L was combined with 500 mL of M.

TABLE 3

Composition of HM media
c) HM medium

| Solution | Preparation† | Final concentration |
|---|---|---|
| A | In 498 mL H$_2$O | |
| (NH$_4$)$_2$SO4 | 1.75 g | 1.75 g/L |
| MgSO$_4$•7H$_2$O | 0.1 g | 0.1 g/L |
| FeSO$_4$•7H$_2$O | 0.02 g | 20 mg/L |
| CaCl$_2$•2H$_2$O | 0.02 g | 20 mg/L |
| B | In 100 mL H$_2$O | |
| Na$_2$MoO$_4$•2H$_2$O | 0.004 g | 0.04 mg/L |
| CuCl$_2$•2H$_2$O | 0.0027 g | 0.027 mg/L |
| c | In 50 mL H$_2$O | |
| MnCl$_2$•4H$_2$0 | 0.18 g | 3.6 mg/L |
| ZnSO$_4$•7H$_2$O | 0.075 g | 1.5 mg/L |
| CoCl$_2$•6H$_2$O | 0.03 g | 0.6 mg/L |
| H$_3$BO$_3$ | 0.01 g | 0.2 mg/L |
| D | In 500 mL H$_2$O | |
| KH$_2$PO$_4$ | 0.68 g | 0.68 g/L |
| Na$_2$HPO$_4$•2H$_2$O | 3.051 g | 3.05 g/L |

†498 mL of A was mixed with 1 mL each of B and C. This mixture was autoclaved, while 500 mL of D was adjusted to pH 7.0 prior to autoclaving. After cooling, 500 mL of A + B + C was combined with 500 mL of D.

TABLE 4

Composition of MM media
d) MM medium

| Solution | Preparation[†] | Final concentration |
|---|---|---|
| E | In 983.5 mL H$_2$O | |
| NaNO3 | 2.0 g | 0.002 g/L |
| F | In 100 mL H$_2$O | |
| KH$_2$PO$_4$ | 13.6 g | 0.884 g/L |
| NaOH | 2.88 g | 0.1872 g/L |
| G | In 1000 mL H$_2$O | |
| MgSO$_4$•7H$_2$O | 20.0 g | 0.2 g/L |
| CaCl$_2$•2H$_2$O | 2.0 g | 0.02 g/L |
| ZnSO$_4$•7H$_2$O | 0.049 g | 0.49 mg/L |
| CuCl$_2$•2H$_2$O | 0.002 g | 0.02 mg/L |
| H3BO3 | 0.006 g | 0.06 mg/L |
| MnCl$_2$•4H$_2$O | 0.0027 g | 0.027 mg/L |
| FeSO$_4$•7H$_2$O | 1.0 g | 0.01 g/L |

[†]983.5 mL of E was mixed with 10 mL of G and autoclaved, while 100 mL of F was adjusted to pH 7.1 and autoclaved. After cooling, 993.5 mL of E + G was combined with 6.5 mL of F.

Figure 4:
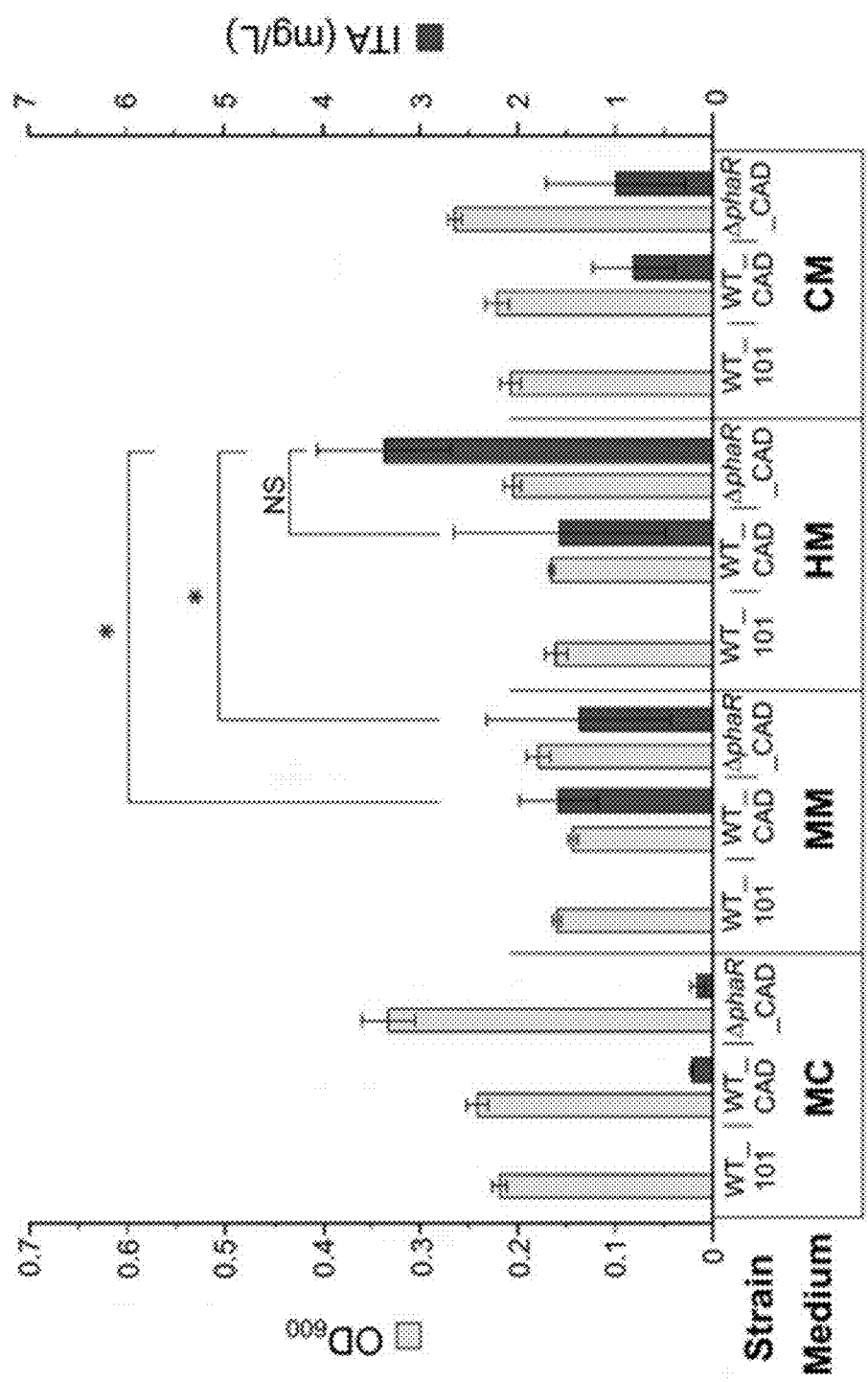
FIG. 4 is a bar graph showing the cell biomass concentration, i.e. optical density at 600 nm wavelength ($OD_{600}$), and itaconic acid (ITA) production in wildtype *Methylorubrum extorquens* AM1 (WT_101 strain), wildtype *Methylorubrum extorquens* AM1 expressing a heterologous codon-optimized gene encoding cis-aconitic decarboxylase (CAD) (WT_CAD strain), and mutant *Methylorubrum extorquens* AM1 with a truncated phaR gene expressing a heterologous codon-optimized gene encoding CAD (ΔphaR_CAD strain) grown in different media, including MC medium, MM medium, HM medium and CM medium with 5 mM sodium acetate used as a carbon substrate in accordance with an example embodiment. (An asterisk denotes significant difference (Student's t-test, $p<0.05$), NS denotes no statistically significant difference, error bars represent one standard deviation).

The inoculum from a 2-day-old culture was added to 50 mL medium to an OD$_{600}$ of 0.02 at the start of an experiment where sodium acetate (5 or 30 mM), disodium succinate (15 mM) or methanol (240 mM) was used as a carbon substrate or source (as shown in FIG. 4). Triplicate biological cultures were prepared for batch experiments. Antibiotics at the following concentrations were used when required for selective culture: kanamycin at 50 µg/mL, tetracycline at 15 µg/mL, and 10-20 µg/mL. Cell culture OD$_{600}$ was measured using a spectrophotometer (SpectraMax M2e, Molecular Devices, United States).

The growth rate and doubling time of *Methylorubrum extorquens* AM1 carrying pTE101 plasmid (WT_101 strain), wildtype *Methylorubrum extorquens* AM1 expressing a heterologous codon-optimized gene encoding cis-aconitic decarboxylase (CAD) (WT_CAD strain), and mutant *Methylorubrum extorquens* AM1 with a truncated phaR gene expressing a heterologous codon-optimized gene encoding CAD (ΔphaR_CAD strain) calculated based on the initial 2-day period during exponential growth is shown in Table 5 below.

TABLE 5

Growth rate and doubling time of the strains

| Strain[a] | Growth rate (h$^{-1}$)[b] | Doubling time (h)[c] |
|---|---|---|
| WT_101 | 0.0753 ± 0.004 | 9.31 ± 0.56 |
| WT_CAD | 0.0760 ± 0.002 | 9.12 ± 0.27 |
| ΔphaR_CAD | 0.0593 ± 0.007 | 11.8 ± 1.25 |

[a]Strains were grown as batch culture in the HM medium with 240 mM methanol as the carbon substrate
[b,c]The growth rate and doubling time were calculated based on the initial 2-day period during exponential growth

Example 2

Metabolic Engineering of *Methylorubrum extorquens* AM1 Strains

Plasmids and sequences of the primers used are listed in Table 6. The gene encoding cis-aconitic acid decarboxylase (CAD) was based on the amino acid sequence of the enzyme from *A. terreus* (GenBank accession no. BAG49047.1) (SEQ ID NO: 4) and was codon optimized using the Codon Optimization OnLine (COOL) software according to the codon usage of 184 genes that were deemed significantly expressed in AM1 (SEQ ID NO: 1). Molecular cloning work was performed with *E. coli* TOP10. The cad gene was excised from pUC57-CAD with VspI and HindIII, and was subsequently ligated into the pTE102 plasmid at the same restriction sites, creating pTE102-CAD where the cad gene was downstream of a ribosomal binding site sequence which worked efficiently in AM1. SEQ ID NO: 3 is a cloned sequence derived from pTE102. The pMxaF promoter region (SEQ ID NO: 3) from pTE102 was excised with BglII and EcoRI, and ligated into pTE101 at the same restriction sites to create pTE101a. Subsequently, the cad assembly from pTE102-CAD was excised using XbaI and PstI and inserted downstream of the pMxaF promoter in the pTE101a via ligation at the SpeI and PstI sites to create pTE101a-CAD. This final expression construct was electroporated into AM1.

TABLE 6

Strains and plasmids used

| Strain | Genotype |
|---|---|
| *Methylorubrum extorquens* AM1 | Wildtype |
| WT_101 | *Methylorubrum extorquens* AM1 carrying pTE101 plasmid |
| WT_CAD | *Methylorubrum extorquens* AM1 carrying pTE101a-CAD plasmid |
| ΔphaR | *Methylorubrum extorquens* AM1 with phaR gene truncated from nucleotide position of 269 to 599 |
| ΔphaR_CAD | ΔphaR strain carrying pTE101a-CAD plasmid |

| Plasmid | Characteristic |
|---|---|
| pUC57-CAD | Chemically synthesized codon optimized cad gene in pUC57 vector, Ap$^R$ |
| pMiniT | Linearized cloning vector, Ap$^R$ |
| pTE101 | Brick vector, no promoter, Km$^R$ |
| pTE102 | Brick vector, mxaF promoter (pMxaF), Tc$^R$ |
| pTE102-CAD | pTE102 plasmid with cad gene inserted downstream of a ribosomal binding site |
| pTE101a | pTE101 plasmid containing pMxaF |
| pTE101a-CAD | pTE101a plasmid with pMxaF: cad |

TABLE 6-continued

| | Strains and plasmids used |
|---|---|
| pCM433 | sacB-based allelic exchange vector, $Ap^R$ $Cm^R$ $Tc^R$ |
| p433-phaR-UD | pCM433 plasmid containing upstream and downstream DNA regions of phaR gene section, for creating the ΔphaR strain |

To create the phaR mutation with in-frame truncation (by excising 339 bp out of the entire gene length of 612 bp) (SEQ ID NO: 2), a DNA region was amplified by the phaR_Up-F (SEQ ID NO: 5) and phaR_Up-R (SEQ ID NO: 6) primers from the AM1 gDNA and cloned into pMiniT (New England BioLabs, United States). A fragment of this construct was excised with XhoI and PstI and cloned into pCM433 at the same restriction sites. After that, the PCR product amplified from gDNA using the phaR_Down-F (SEQ ID NO: 7) and phaR_Down-R (SEQ ID NO: 8) primers was directly cloned into the pCM433-based construct above at the PstI and VspI sites, creating the allelic exchange plasmid p433-phaR-UD. This plasmid was conjugated into AM1 by *E. coli* S17-1 λpir. Mutant colonies (i.e., ΔphaR strain) were screened for sensitivity to tetracycline and verified by PCR.

PCR amplification was performed with the Accura High-Fidelity Polymerase (Lucigen, United States), while restriction enzymes and T4 DNA ligase were purchased from New England BioLabs (United States) and Promega (United States).

Analytic Measurements

Itaconic acid, acetate, and methanol were measured using liquid chromatography equipped with a photodiode array detector (210 nm wavelength) and a refractive index detector (35° C.) (ACQUITY UPLC, Waters Corporation, United States). The Aminex Ion Exclusion HPX-87H column (65° C.) (Bio-Rad, United States) with 5 mM $H_2SO_4$ mobile phase (0.4 mL/min) was used.

Poly-β-hydroxybutyric acid (PHB) analysis was carried out. Briefly, the cell pellet was first dried overnight at 55° C. Concentrated $H_2SO_4$ (1 mL) was added to the sample and boiled at 120° C. for 40 min. Subsequently, 4 mL of 7 mM $H_2SO_4$ was added and the solution was filtered before liquid chromatography analysis with the same conditions as above except 7 mM $H_2SO_4$ was used as the mobile phase. PHB standards (Sigma-Aldrich, United States) were subjected to the same treatment as the samples.

Example 3

RNA Extraction and Sequencing

For each sample for RNA-Seq, three bottles of culture grown in 50 mL HM medium containing 240 mM methanol and kanamycin ($OD_{600}$=0.5-0.6) were pooled and 100 mL was used for RNA extraction. The cells were pelleted by centrifugation at 10,000 rpm for 10 min, snap frozen with liquid nitrogen and immediately stored at −80° C. Total RNA was extracted using the RNeasy Mini kit (Qiagen, Germany) after cell lysis with lysozyme (7.5 mg/mL) (Sigma-Aldrich, United States) for 10 min, followed by homogenization using the Mini-Beadbeater-16 (BioSpec Products, United States) with autoclaved 0.1 mm zirconia/silica beads (BioSpec Products, United States) for 5 min. gDNA removal with DNase (Qiagen, Germany) was performed according to the manufacturer's instructions. rRNA removal was performed using the Ribo-Zero Magnetic Kit (Illumina, United States) and the rRNA-depleted RNA samples were used as templates to create cDNA libraries containing 250-300 bp inserts with the NEBNext Ultra Directional RNA Library Prep Kit for Illumina sequencing (New England BioLabs, United States). Paired-end sequencing (150 bp) was performed using the Illumina HiSeq 4000 sequencing platform, generating about 1 Gb of raw data per sample. Three biological replicates of each strain were prepared for RNA-Seq.

Analysis of RNA-Seq Data

Raw sequencing reads were subjected to quality control using FastQC v0.11.5 and illumina-utils v2.0.2 following best practice criteria for RNA-Seq analysis. High-quality reads were pseudo-aligned to the AM1 gene sequences (GCF_000022685.1) using kallisto v0.43.1 with 100 bootstraps per sample. Differential expression was analyzed using sleuth v0.29.0 with integration of bootstraps from the pseudo-alignment. Transcript level was reported as Transcripts Per Million (TPM). The Wald test was used to assess the differential expression of transcripts and the transformation function $log_2(x+0.5)$ was passed to sleuth quantification to calculate the effect size (β value) as $log_2$-based fold changes. $Log_2$-based fold changes of less than −1 or greater than 1, in conjunction with a false discovery rate-adjusted p-value<0.01, were used as the threshold for identifying significant differential gene expression. Gene expression profiles were analyzed by comparing WT_CAD against WT_101, phaR_CAD against WT_101 and ΔphaR_CAD against WT_CAD. Unless otherwise indicated, all the genes described were significantly differential expressed. KEGG Orthology assignment was made using BlastKOALA and gene ontology was obtained with eggNOG-mapper. Gene locus tags are based on the following RefSeq sequences: *Methylorubrum extorquens* AM1 chromosome (NC_012808.1), and the four plasmids of *Methylorubrum extorquens* AM1 [megaplasmid (NC_012811.1), p1 META1 (NC_012807.1), p2META1 (NC_012809.1), and p3META1 (NC_012810.1)].

Example 4

Bioreactor Experiments

A twin 2 L Biostat B stirred tank bioreactor (Sartorius Stedim, France) was used. As inoculum, 100 mL seed culture grown in HM with 124 mM methanol and kanamycin for 3 days was transferred into the bioreactor vessel containing 1 L of HM with 240 mM methanol and kanamycin, resulting in an initial $OD_{600}$ of ~0.1. After 24 h of cultivation, 2.5 or 5 mL pure methanol was added periodically using a variable-speed peristaltic pump to achieve a target methanol concentration of 240 mM. Antifoam C Emulsion (Sigma-Aldrich, United States) was added manually when necessary to prevent excessive foam formation. The incubation temperature of 30° C. was maintained with a water jacket, while a pH of 7.0 was maintained with either 1 M ammonium hydroxide ($NH_4OH$) or 1 M sodium hydroxide (NaOH). Dissolved oxygen concentration was maintained by the variable impeller (200-700 rpm) and compressed air (up to 1 L/min). Bioreactor experiments were performed in duplicate for each condition.

Example 5

Results

To produce ITA by AM1, the inventors engineered the wildtype to express a heterologous codon-optimized gene encoding cad from *A. terreus* that converts cis-aconitic acid to ITA. The CAD-encoding gene (cad) was controlled by the pMxaF constitutive promoter in the high-copy number pTE101-based plasmid.

*Methylorubrum extorquens* AM1 strain is advantageously a suitable platform for itaconic acid production as the strain is highly tolerant to the inhibitory effect of itaconic acid (10 mM) which inhibits isocitrate lyase. With reference to FIG. 1, *Methylorubrum extorquens* AM1 employs the EMC pathway for glyoxylate regeneration and does not utilize itaconic acid as a carbon substrate.

Figure 2:
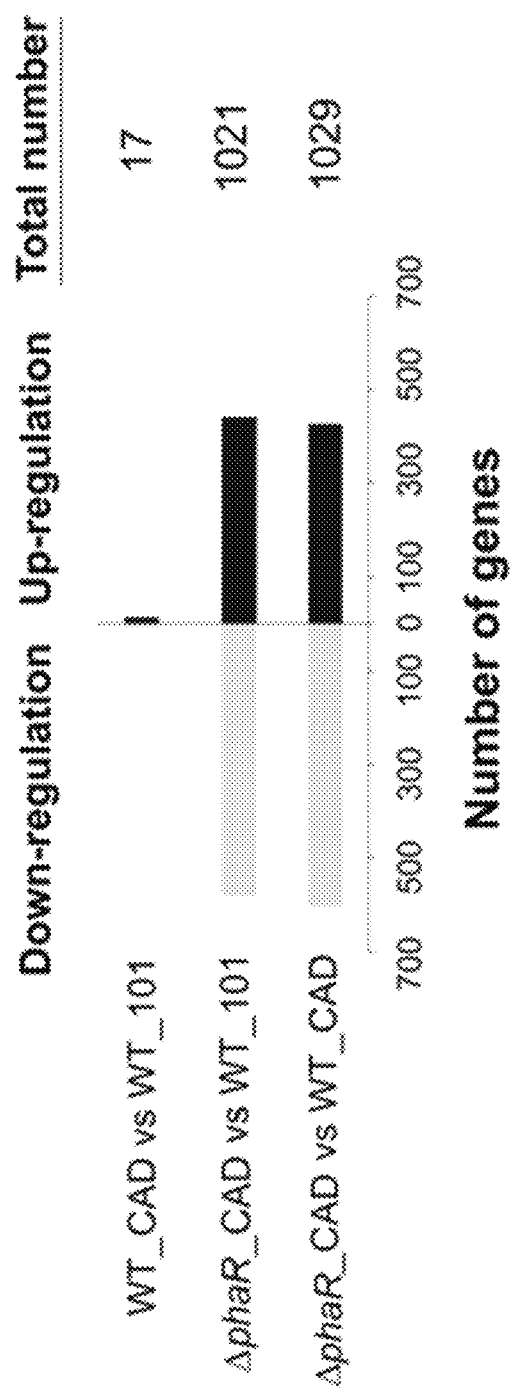
FIG. 2 is a comparison of the number of up-regulated and down-regulated genes between wildtype *Methylorubrum extorquens* AM1 carrying a pTE101 plasmid (WT_101), wildtype *Methylorubrum extorquens* AM1 expressing a heterologous codon-optimized gene encoding cis-aconitic decarboxylase (CAD) (WT_CAD) and mutant *Methylorubrum extorquens* AM1 with a truncated phaR gene expressing a heterologous codon-optimized gene encoding CAD (ΔphaR_CAD) in accordance with an example embodiment.
Figure 3:
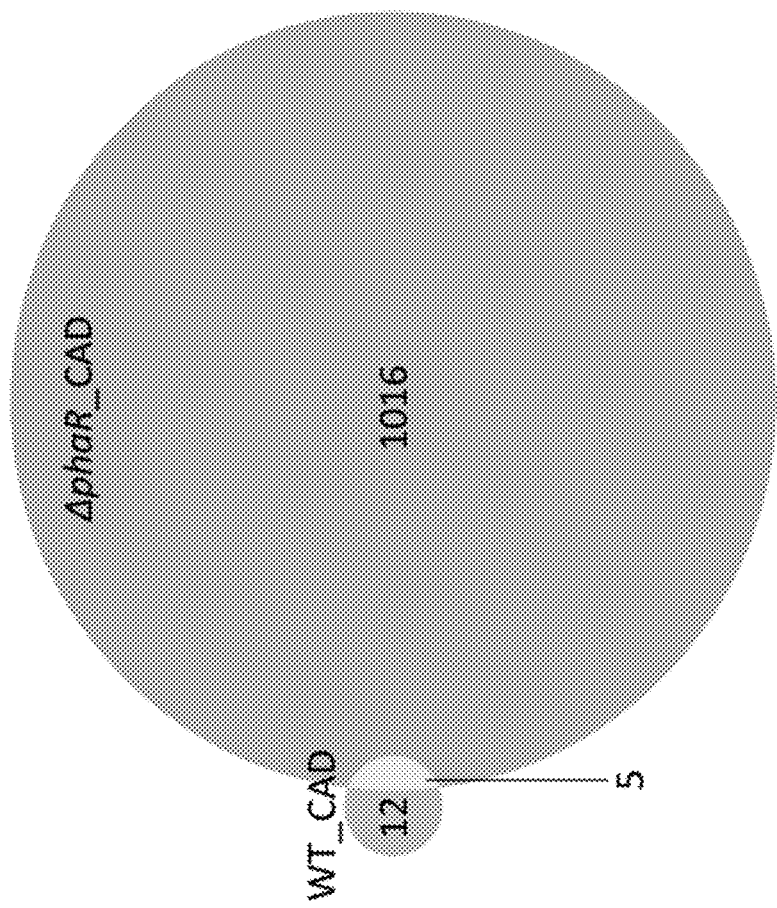
FIG. 3 is a Venn diagram showing the number of shared differentially expressed genes between WT_CAD and ΔphaR_CAD relative to WT_101 in accordance with an example embodiment.

With reference to FIG. 2, the number of up-regulated and down-regulated genes in the wildtype *Methylorubrum extorquens* AM1 carrying a pTE101 plasmid (WT_101), wildtype *Methylorubrum extorquens* AM1 expressing a heterologous codon-optimized gene encoding cis-aconitic decarboxylase (CAD) (WT_CAD) and mutant *Methylorubrum extorquens* AM1 with a truncated phaR gene expressing a heterologous codon-optimized gene encoding CAD (ΔphaR_CAD) is shown and FIG. 3 illustrates that the number of shared differentially expressed genes in ΔphaR_CAD and WT_CAD with 5 genes commonly shared in these strains.

Turning to FIG. 4, using 5 mM sodium acetate as a carbon substrate, cell biomass concentration ($OD_{600}$) and itaconic acid (ITA) production was compared between the WT_101, WT_CAD and ΔphaR_CAD strains in the MC, MM, HM and CM mediums. Samples were taken at the end of the cultivation period on day 8 after acetate was completely consumed. WT_CAD which corresponds to a recombinant cell comprising the first polynucleotide sequence as defined in SEQ ID NO: 1 or a homologue thereof operably linked to a regulatory sequence, and ΔphaR_CAD which corresponds to a recombinant cell comprising the first polynucleotide sequence and the second polynucleotide sequence both produced itaconic acid compared to WT_101 that lacked a protein or fragment having CAD activity.

Figure 5A:
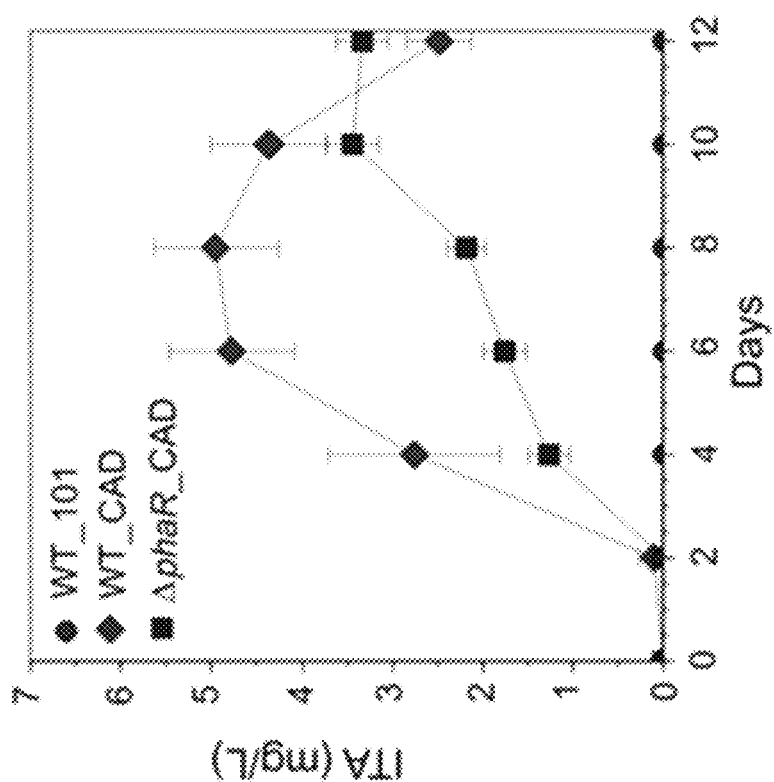
FIG. 5A is a line graph showing the ITA concentration in WT_101, WT_CAD, and ΔphaR_CAD strains of *Methylorubrum extorquens* AM1 grown in HM medium supplemented with 30 mM sodium acetate as the carbon substrate in accordance with an example embodiment. (Error bars represent one standard deviation).
Figure 5B:
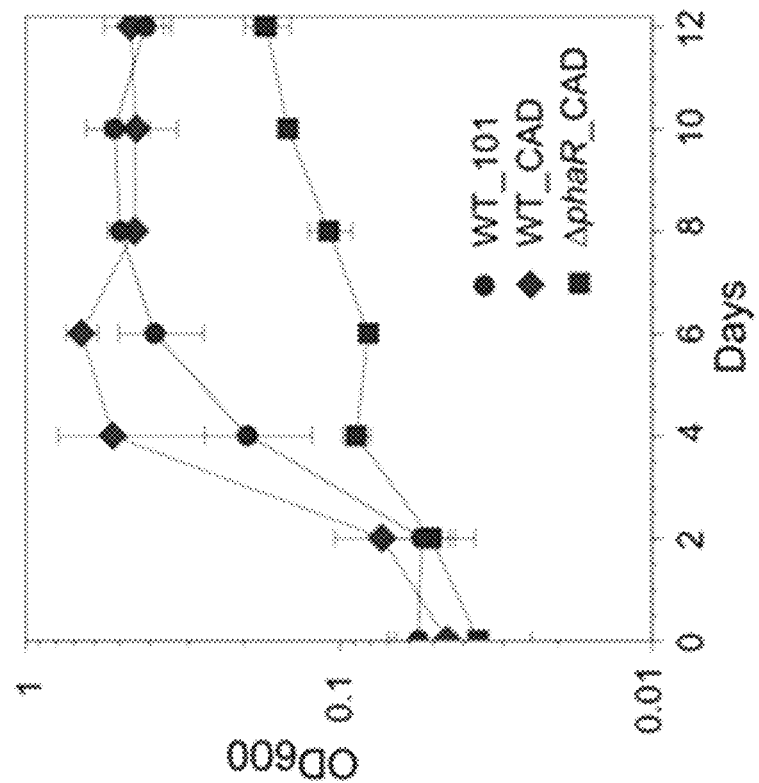
FIG. 5B is a line graph showing optical density ($OD_{600}$) in WT_101, WT_CAD, and ΔphaR_CAD strains of *Methylorubrum extorquens* AM1 grown in HM medium supplemented with 30 mM sodium acetate as the carbon substrate in accordance with an example embodiment. (Error bars represent one standard deviation).
Figure 5C:
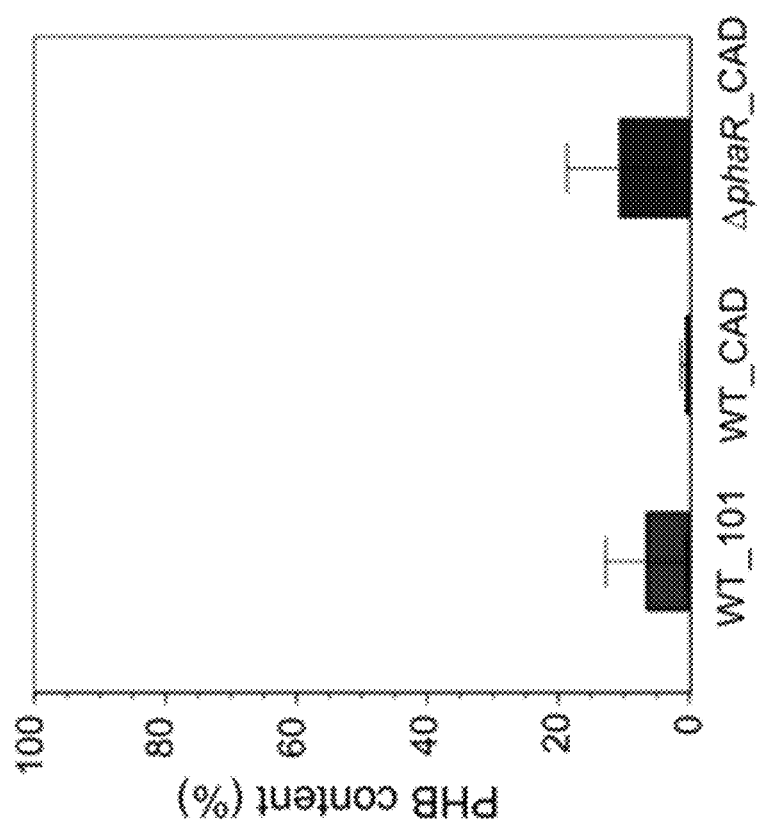
FIG. 5C is a line graph showing poly-β-hydroxybutyric acid (PHB) content (%, PHB weight/cell dry weight) in WT_101, WT_CAD, and ΔphaR_CAD strains of *Methylorubrum extorquens* AM1 grown in HM medium supplemented with 30 mM sodium acetate as the carbon substrate in accordance with an example embodiment. PHB content was measured on day 12 after acetate was mostly consumed.

FIGS. 5A-5C illustrate the WT_101, WT_CAD and ΔphaR_CAD strains grown in HM medium supplemented with 30 mM acetate as the carbon substrate. FIG. 5A shows itaconic acid (ITA) production wherein WT_CAD produces the highest concentration of ITA (mg/L), particularly at day 8, and also shows ΔphaR_CAD strain's highest ITA production on day 10. FIG. 5B shows $OD_{600}$ with the WT_CAD having a high growth rate. In FIG. 5C the PHB content (%) is shown after being measured on day 12 after the acetate was consumed, with the WT_CAD strain accumulating the least amount of PHB. This data shows that the WT_CAD and ΔphaR_CAD strains are well suited to the production of ITA.

Figure 6D:
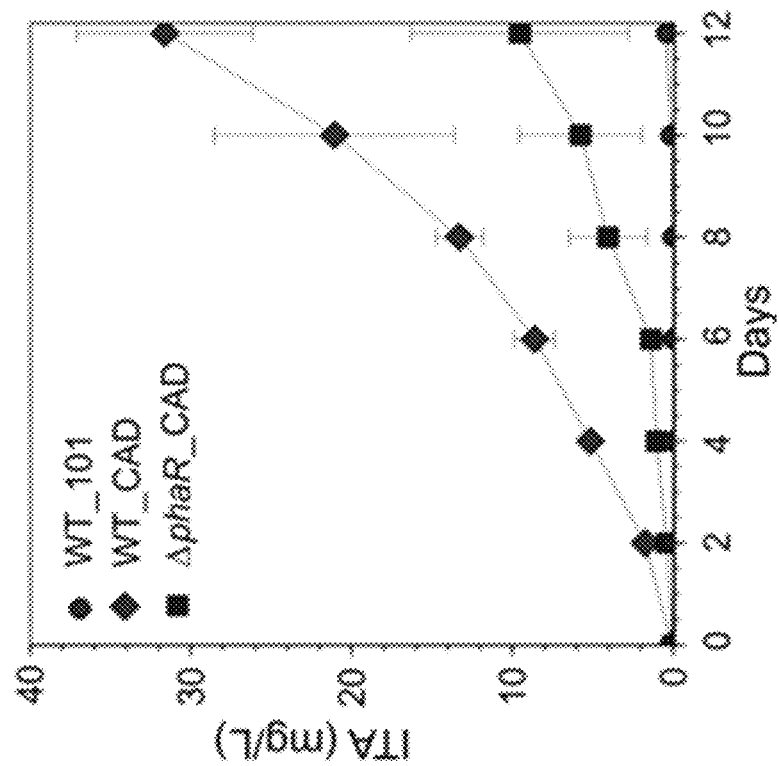
FIG. 6D is a line graph showing ITA concentration in WT_101, WT_CAD, and ΔphaR_CAD strains of *Methylorubrum extorquens* AM1 grown in HM medium supplemented with 240 mM methanol as the carbon substrate in accordance with an example embodiment.
Figure 6C:
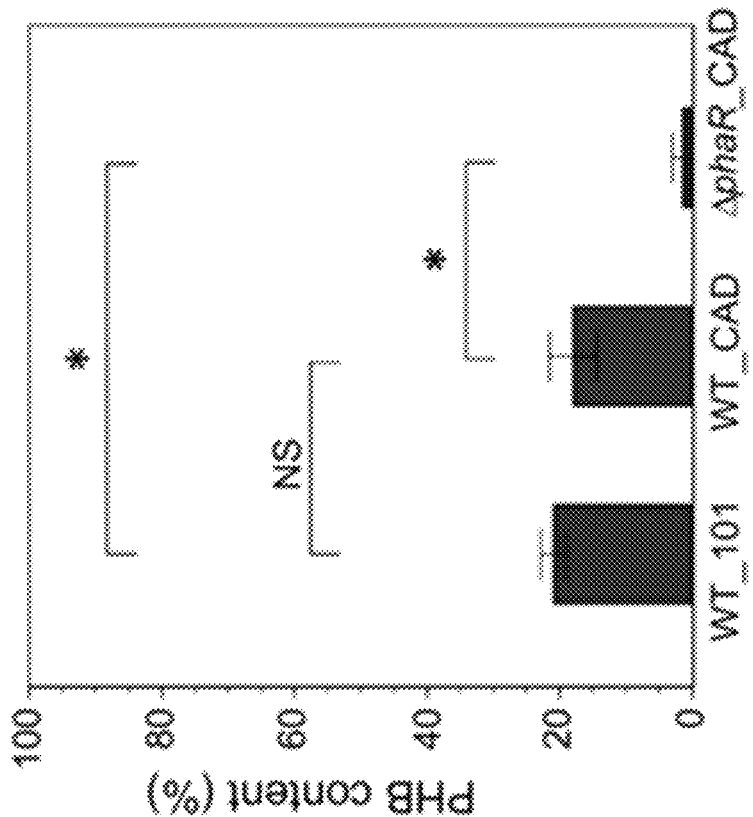
FIG. 6C is a bar graph showing PHB content (%, PHB weight/cell dry weight) measured at the final time point in WT_101, WT_CAD, and ΔphaR_CAD strains of *Methylorubrum extorquens* AM1 grown in HM medium supplemented with 240 mM methanol as the carbon substrate in accordance with an example embodiment.

FIGS. 6A-6D illustrate the WT_101, WT_CAD and ΔphaR_CAD strains grown in HM medium supplemented with 240 mM methanol as the carbon substrate. FIG. 6A shows the cell biomass ($OD_{600}$) and FIG. 6B shows the percentage of remaining methanol over time. Exponential growth and methanol consumption were high in WT_CAD strains reaffirming the advantage of this strain in the production of itaconic acid. FIGS. 6C and 6D show PHB content and ITA production, respectively and further illustrate the suitability of the WT_CAD strain and ΔphaR_CAD strain for producing ITA.

Figure 7A:
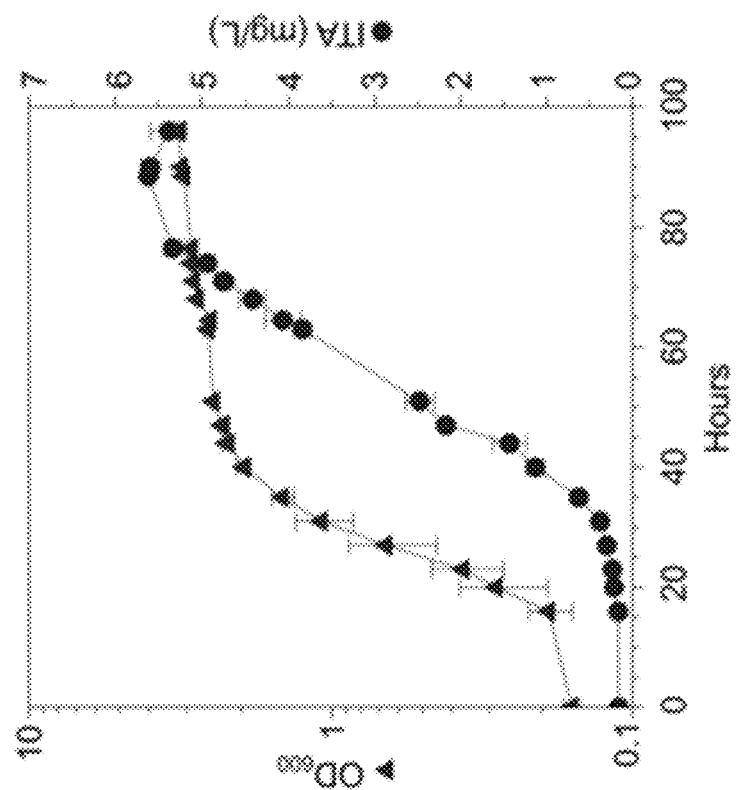
FIG. 7A is a line graph showing optical density ($OD_{600}$) and ITA concentration from a fed-batch bioreactor experiment of WT_CAD strain of *Methylorubrum extorquens* AM1 grown in HM medium with methanol as a carbon substrate and dissolved oxygen saturation level maintained at 25% and pH control with 1 M NaOH, in accordance with an example embodiment.
Figure 7B:
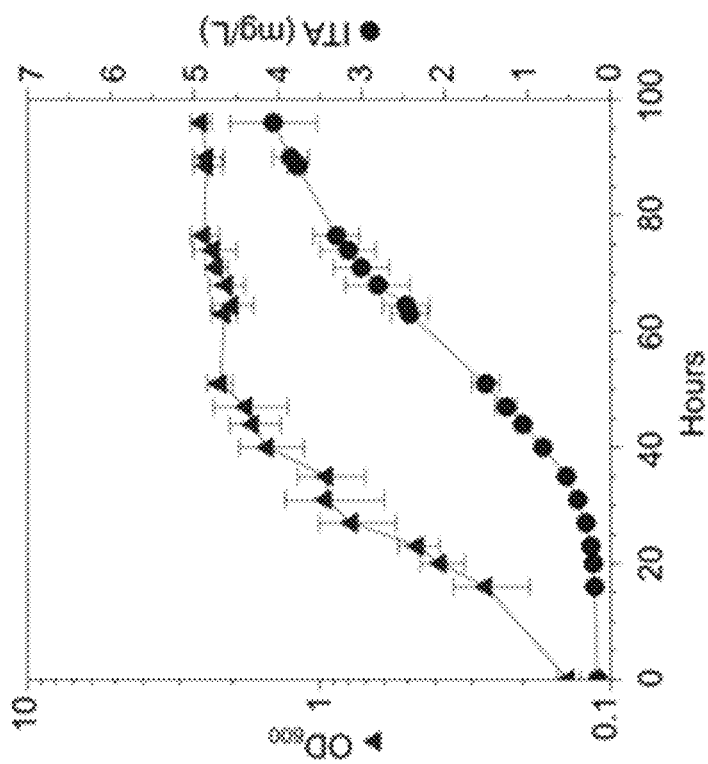
FIG. 7B is a line graph showing optical density ($OD_{600}$) and ITA concentration from a fed-batch bioreactor experiment of WT_CAD strain of *Methylorubrum extorquens* AM1 grown in HM medium with methanol as a carbon substrate and dissolved oxygen saturation level maintained at 60% and pH control with 1 M $NH_4OH$.

FIGS. 7A and 7B illustrate fed-batch bioreactor experiments of WT_CAD grown in HM medium with methanol as the carbon substrate. Dissolved oxygen saturation level was maintained at 25% and pH controlled with 1 M NaOH in FIG. 7A. Dissolved oxygen saturation level was maintained at 60% and pH controlled with 1 M $NH_4OH$ in FIG. 7B. A high concentration of ITA was produced at both oxygen saturation levels, with a higher concentration of ITA produced with an oxygen saturation level of 60%.

The examples and results demonstrate the suitability of the recombinant cell of the genus *Methylorubrum* that includes a first polynucleotide sequence as defined in SEQ ID NO: 1 or a homologue thereof operably linked to a regulatory sequence to the production of ITA. The present invention provides a method of producing ITA using a recombinant cell that is inexpensive, reliable and efficient.

The invention claimed is:

1. A recombinant cell comprising a first polynucleotide encoding a protein or fragment thereof having cis-aconitic acid decarboxylase (CAD) activity for producing itaconic acid from a carbon substrate, wherein the first polynucleotide comprises SEQ ID NO: 1 operably linked to a regulatory sequence, and the recombinant cell is of the genus *Methylorubrum*.

2. The recombinant cell of claim 1, further comprising a second polynucleotide, wherein the second polynucleotide comprises SEQ ID NO: 2.

3. The recombinant cell of claim 1, wherein the carbon substrate is selected from the group consisting of methanol, methylamine, formate, pyruvate, succinate, lactate and acetate.

4. The recombinant cell of claim 1, wherein the carbon substrate is selected from the group consisting of acetate, succinate and methanol.

5. The recombinant cell of claim 1, wherein the carbon substrate is methanol.

6. The recombinant cell of claim 1, wherein the recombinant cell is *Methylorubrum extorquens*.

7. The recombinant cell of claim 1, wherein the recombinant cell is *Methylorubrum extorquens* AM1.

8. The recombinant cell of claim 1, wherein the regulatory sequence is a promoter comprising SEQ ID NO: 3.

9. The recombinant cell of claim 1, wherein the CAD is one derivable from or found in *Aspergillus terreus*.

10. A method of producing itaconic acid using a recombinant cell, wherein the recombinant cell comprises a first polynucleotide encoding a protein or a fragment thereof having cis-aconitic acid decarboxylase (CAD) activity for producing itaconic acid from a carbon substrate, wherein the first polynucleotide comprises SEQ ID NO: 1, wherein said method comprises the step of incubating the recombinant cell in a medium containing a carbon substrate for producing itaconic acid.

11. The method of claim 10, wherein the recombinant cell further comprises a second polynucleotide, wherein the second polynucleotide comprises SEQ ID NO: 2.

12. The method of claim 10, wherein the carbon substrate is selected from the group consisting of methanol, methylamine, formate, pyruvate, succinate, lactate and acetate.

13. The method of claim 10, wherein the carbon substrate is selected from the group consisting of acetate, succinate and methanol.

14. The method of claim 10, wherein the carbon substrate is methanol.

15. The method of claim 10, wherein the recombinant cell is *Methylorubrum extorquens*.

16. The method of claim 10, wherein the recombinant cell is *Methylorubrum extorquens* AM1.

17. The method of claim 10, wherein the regulatory sequence is a promoter comprising SEQ ID NO: 3.

18. The method of claim 10, wherein the CAD is one derivable from or found in *Aspergillus terreus*.

* * * * *

SEQUENCE LISTING

```
<160> NUMBER OF SEQ ID NOS: 9

<210> SEQ ID NO 1
<211> LENGTH: 1473
<212> TYPE: DNA
<213> ORGANISM: Artificial Sequence
<220> FEATURE:
<223> OTHER INFORMATION: Synthesized

<400> SEQUENCE: 1
atgaccaagc agtccgccga ttcgaacgcc aagtcgggcg tcacgagcga gatctgccac      60
tgggcctcga acctggccac cgacgatatc ccctccgacg tgctggaacg cgcgaagtac     120
ctgatccttg acggcatcgc ctgcgcctgg gtcggcgcac gagtgccctg gagcgagaag     180
```

```
tacgtccagg caacgatgag cttcgagccg ccgggcgcgt gccgcgtcat cgggtacggc      240
cagaagctgg ggccggtggc cgccgctatg acgaactcgg ccttcatcca ggcgaccgag      300
ctcgacgact accactccga agcaccgctg cattccgcct cgatcgtcct cccggccgtc      360
ttcgcggcca gtgaggtgtt ggccgagcag ggcaagacca tctccggcat cgacgtgatc      420
ctcgctgcga tcgtaggctt cgagtccggc cccaggatcg gcaaggccat ctacggctcg      480
gacctcctga caacggctg gcactgcggg gccgtctacg gtgccccggc gggcgccctg      540
gcgacgggca agctcctcgg cctgacgccg gactccatgg aagatgcctt aggtatcgcc      600
tgcacccagg cctgcggcct gatgtcgcg cagtacggcg catggtcaa gcgcgtccag        660 cacgggttcg ccgctaggaa cgggttgctt ggcggcctcc tggcccacgg tggttacgag      720
gcgatgaagg gcgtgctgga gcgctcttac ggcggcttcc tgaagatgtt caccaagggc      780
aacggacggg agccgcccta caaagaggaa gaggtcgtcg cgggcctggg cagcttctgg      840
cacaccttca cgattcggat caagctctat gcgtgctgcg gcttggtgca cggtccggtt      900
gaggccatcg agaacctcca gggccgctac ccggaactcc tgaaccgcgc caacctgtcc      960
aacatccggc atgtccacgt ccagctgagc accgcctcga actcgcattg cggctggatc     1020
cccgaggagc gtccgatctc gtccattgcc ggccagatgt cggtggcgta tatcctggcg     1080
gtgcagctcg tcgaccagca gtgcctgctc agccagttct cggagttcga tgacaacctt     1140
gagcggcctg aagtctggga cctcgcccgc aaggtcacct cctcgcagag cgaggagttc     1200
gaccaggacg gcaactgcct cagcgcaggc cgcgtgagga tcgagttcaa cgacggctcc     1260
tccatcacga atcggtcga gaagcccctg ggcgtcaagg agccgatgcc gaacgagcgc      1320
atcctgcaca gtaccgcac gctggcgggt tcggtcacgg acgagtcccg cgtcaaggag      1380
atcgaggatc tcgtgctggg cctggatcgc ctcaccgaca tctcaccgct tctcgagctg     1440
ctcaactgcc cggtcaagag cccgctggtg tga                                  1473

<210> SEQ ID NO 2
<211> LENGTH: 279
<212> TYPE: DNA
<213> ORGANISM: Artificial Sequence
<220> FEATURE:
<223> OTHER INFORMATION: Gene truncation modification

<400> SEQUENCE: 2
atggccgaga acggcagggc gcatcagacc gtcatcaaga agtacgccaa tcgccggctc       60
tatcacaccg gcacctccac ctacgtcacg ctcgaagacc tcgcgacgat ggtgcagaac      120
ggcgaagact tcatcgtcta cgacgcacgc tcgggcgacg acatcacccg ctcggtgctg      180
acgcagatca tcttcgagca ggagaacaag gccggcgacg acaatctgct gccggtggcc      240
ttcctgcggc agctgatccg cttctacgct gcagagtag                             279

<210> SEQ ID NO 3
<211> LENGTH: 40
<212> TYPE: DNA
<213> ORGANISM: Artificial Sequence
<220> FEATURE:
<223> OTHER INFORMATION: Derived from pTE102 plasmid

<400> SEQUENCE: 3
gctaaagaca tcgcgtccaa tcaaagccta gaaaatatag                             40

<210> SEQ ID NO 4
<211> LENGTH: 490
```

<212> TYPE: PRT
<213> ORGANISM: Artificial Sequence
<220> FEATURE:
<223> OTHER INFORMATION: Synthesized

<400> SEQUENCE: 4

```
Met Thr Lys Gln Ser Ala Asp Ser Asn Ala Lys Ser Gly Val Thr Ser
1               5                   10                  15

Glu Ile Cys His Trp Ala Ser Asn Leu Ala Thr Asp Asp Ile Pro Ser
            20                  25                  30

Asp Val Leu Glu Arg Ala Lys Tyr Leu Ile Leu Asp Gly Ile Ala Cys
        35                  40                  45

Ala Trp Val Gly Ala Arg Val Pro Trp Ser Glu Lys Tyr Val Gln Ala
    50                  55                  60

Thr Met Ser Phe Glu Pro Pro Gly Ala Cys Arg Val Ile Gly Tyr Gly
65                  70                  75                  80

Gln Lys Leu Gly Pro Val Ala Ala Ala Met Thr Asn Ser Ala Phe Ile
            85                  90                  95

Gln Ala Thr Glu Leu Asp Asp Tyr His Ser Glu Ala Pro Leu His Ser
            100                 105                 110

Ala Ser Ile Val Leu Pro Ala Val Phe Ala Ala Ser Glu Val Leu Ala
            115                 120                 125

Glu Gln Gly Lys Thr Ile Ser Gly Ile Asp Val Ile Leu Ala Ala Ile
130                 135                 140

Val Gly Phe Glu Ser Gly Pro Arg Ile Gly Lys Ala Ile Tyr Gly Ser
145                 150                 155                 160

Asp Leu Leu Asn Asn Gly Trp His Cys Gly Ala Val Tyr Gly Ala Pro
            165                 170                 175

Ala Gly Ala Leu Ala Thr Gly Lys Leu Leu Gly Leu Thr Pro Asp Ser
            180                 185                 190

Met Glu Asp Ala Leu Gly Ile Ala Cys Thr Gln Ala Cys Gly Leu Met
            195                 200                 205

Ser Ala Gln Tyr Gly Gly Met Val Lys Arg Val Gln His Gly Phe Ala
210                 215                 220

Ala Arg Asn Gly Leu Leu Gly Gly Leu Leu Ala His Gly Gly Tyr Glu
225                 230                 235                 240

Ala Met Lys Gly Val Leu Glu Arg Ser Tyr Gly Gly Phe Leu Lys Met
            245                 250                 255

Phe Thr Lys Gly Asn Gly Arg Glu Pro Pro Tyr Lys Glu Glu Glu Val
            260                 265                 270

Val Ala Gly Leu Gly Ser Phe Trp His Thr Phe Thr Ile Arg Ile Lys
            275                 280                 285

Leu Tyr Ala Cys Cys Gly Leu Val His Gly Pro Val Glu Ala Ile Glu
            290                 295                 300

Asn Leu Gln Gly Arg Tyr Pro Glu Leu Leu Asn Arg Ala Asn Leu Ser
305                 310                 315                 320

Asn Ile Arg His Val His Val Gln Leu Ser Thr Ala Ser Asn Ser His
            325                 330                 335

Cys Gly Trp Ile Pro Glu Glu Arg Pro Ile Ser Ser Ile Ala Gly Gln
            340                 345                 350

Met Ser Val Ala Tyr Ile Leu Ala Val Gln Leu Val Asp Gln Gln Cys
            355                 360                 365

Leu Leu Ser Gln Phe Ser Glu Phe Asp Asp Asn Leu Glu Arg Pro Glu
            370                 375                 380
```

```
Val Trp Asp Leu Ala Arg Lys Val Thr Ser Ser Gln Ser Glu Glu Phe
385                 390                 395                 400

Asp Gln Asp Gly Asn Cys Leu Ser Ala Gly Arg Val Arg Ile Glu Phe
            405                 410                 415

Asn Asp Gly Ser Ser Ile Thr Glu Ser Val Glu Lys Pro Leu Gly Val
        420                 425                 430

Lys Glu Pro Met Pro Asn Glu Arg Ile Leu His Lys Tyr Arg Thr Leu
        435                 440                 445

Ala Gly Ser Val Thr Asp Glu Ser Arg Val Lys Glu Ile Glu Asp Leu
    450                 455                 460

Val Leu Gly Leu Asp Arg Leu Thr Asp Ile Ser Pro Leu Leu Glu Leu
465                 470                 475                 480

Leu Asn Cys Pro Val Lys Ser Pro Leu Val
                485                 490

<210> SEQ ID NO 5
<211> LENGTH: 25
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (1)..(3)
<223> OTHER INFORMATION: n is a, c, g, t or u

<400> SEQUENCE: 5
nnnggatcct ccgcaccaca tcgac                                   25

<210> SEQ ID NO 6
<211> LENGTH: 25
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (1)..(3)
<223> OTHER INFORMATION: n is a, c, g, t or u

<400> SEQUENCE: 6
nnnctgcaga gtagggcctc gtccc                                   25

<210> SEQ ID NO 7
<211> LENGTH: 27
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (1)..(3)
<223> OTHER INFORMATION: n is a, c, g, t or u

<400> SEQUENCE: 7
nnnctgcagc gtagaagcgg atcagct                                 27

<210> SEQ ID NO 8
<211> LENGTH: 29
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (1)..(3)
```

<223> OTHER INFORMATION: n is a, c, g, t or u

<400> SEQUENCE: 8
nnnattaatc gatatcttca ctggctgcc        29

<210> SEQ ID NO 9
<211> LENGTH: 92
<212> TYPE: PRT
<213> ORGANISM: Artificial Sequence
<220> FEATURE:
<223> OTHER INFORMATION: Synthesized

<400> SEQUENCE: 9

Met Ala Glu Asn Gly Arg Ala His Gln Thr Val Ile Lys Lys Tyr Ala
1               5                   10                  15

Asn Arg Arg Leu Tyr His Thr Gly Thr Ser Thr Tyr Val Thr Leu Glu
            20                  25                  30

Asp Leu Ala Thr Met Val Gln Asn Gly Glu Asp Phe Ile Val Tyr Asp
        35                  40                  45

Ala Arg Ser Gly Asp Asp Ile Thr Arg Ser Val Leu Thr Gln Ile Ile
    50                  55                  60

Phe Glu Gln Glu Asn Lys Ala Gly Asp Asp Asn Leu Leu Pro Val Ala
65                  70                  75                  80

Phe Leu Arg Gln Leu Ile Arg Phe Tyr Ala Ala Glu
                85                  90